United States Patent [19]

Lafon

[11] 4,065,584
[45] Dec. 27, 1977

[54] SULPHUR CONTAINING ARYLAMINE DERIVATIVES

[76] Inventor: Victor Lafon, Paris, France

[21] Appl. No.: 617,664

[22] Filed: Sept. 29, 1975

[30] Foreign Application Priority Data

Sept. 30, 1974 United Kingdom ............... 42387/74

[51] Int. Cl.$^2$ .......................... A01N 9/20; A01N 9/24; C07C 87/02
[52] U.S. Cl. ............................... 424/316; 260/239 B; 260/268 C; 260/293.73; 260/326.12 R; 260/343.7; 260/518 R; 260/570.5 S; 424/244; 424/248.52; 424/250; 424/267; 424/274; 424/330; 544/106
[58] Field of Search ...................... 250/570.5 S, 570.7, 250/561.19

[56] References Cited

U.S. PATENT DOCUMENTS

| | | | |
|---|---|---|---|
| 3,723,524 | 3/1973 | Augsteen et al. | 260/570.5 X |
| 3,789,072 | 1/1974 | Bernstein | 260/570.7 X |
| 3,883,548 | 5/1975 | Hill | 260/570.7 X |

FOREIGN PATENT DOCUMENTS

2,246,429  3/1973  Germany ........................ 260/570.5

OTHER PUBLICATIONS

Nobles et al., "Journal Pharm. Sci." vol. 54, No. 4, pp. 576–580 (1965).

*Primary Examiner*—Robert V. Hines

[57] ABSTRACT

The invention provides new compounds of the formula:

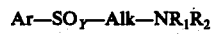

Ar—SO$_Y$—Alk—NR$_1$R$_2$ in which Ar represents a phenyl group, a phenyl group substituted by one or more C$_1$–C$_4$ alkyl, CF$_3$ and COOH groups, or a 2-benzimidazolyl group optionally substituted in the 1-position, $Y$ is 0 or 1, Alk is a C$_2$–C$_5$ hydrocarbon radical with a straight or branched chain, and NR$_1$R$_2$ is a secondary, tertiary or N-heterocyclic amino group, and their addition salts which show pharmacological activity, e.g. as analgesics, anti-inflammatory agents, and anorexigenic agents.

2 Claims, No Drawings

SULPHUR CONTAINING ARYLAMINE DERIVATIVES

The present invention relates to sulphur-containing arylamine derivatives and their production.

French Patent Application No. 72/33,005, published prior to examination under No. 2,154,528, (corresponding to British Specification No. 1371650) discloses, as pharmacologically active substances, sulphur-containing arylamines of the formula:

$$Ar - SO_x - A_o - NR'_1R'_2 \qquad (Io)$$

in which $x$ is 1 or 2, $A_o$ is a $C_2$–$C_4$ alkylene group, $NR'_1R'_2$ represents a secondary, tertiary or N-heterocyclic amino group, and Ar represents an aryl group, a substituted aryl group or a 2-benzimidazolyl group, and their addition salts with acids.

The present invention provides new sulphur-containing products, useful in therapy, especially as analgesic, anti-inflammatory and/or anorexigenic agents, which have the general formula:

$$Ar - SO_y - Alk - NR_1R_2 \qquad (I)$$

in which Ar represents a phenyl group, a phenyl group substituted by one or more $C_1$–$C_4$ alkyl, $CF_3$ and COOH groups, or a 2-benzimidazolyl group optionally substituted in the 1-position, $y$ is 0 or 1, Alk is a $C_2$–$C_5$ hydrocarbon radical with a straight or branched chain and $NR_1R_2$ is a secondary, tertiary or N-heterocyclic amino group, and their addition salts.

More precisely, the present invention provides:

a. The phenylthio-alkylamines which correspond to the general formula:

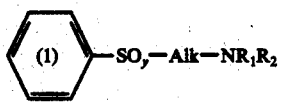

(Ia)

in which $y$ is 0 or 1, Alk represents a $C_2$–$C_5$ hydrocarbon radical with a straight or branched chain, $NR_1R_2$ represents $N(CH_3)_2$, $N(C_2H_5)_2$, $NHCH_2CH_2OH$ or the morpholino, piperidino, pyrrolidino, azepino or 4-ethoxycarbonyl-piperazino groups, and the nucleus (1) is a phenyl group optionally further substituted by one or more $C_1$–$C_4$ alkyl, $CF_3$ and COOH groups, and their addition salts; and b. 1-(p-chlorobenzoyl)-2-($\beta$-morpholinoethylsulphinyl)-benzimidazole, which has the structural formula:

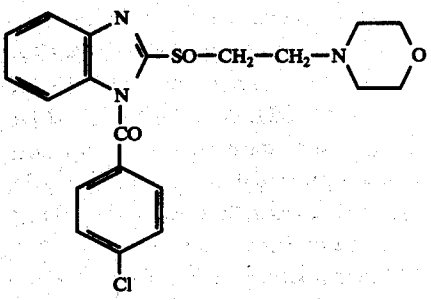

(Ib)

and its addition salts. By addition salts are meant the addition salts with acids, and the ammonium salts.

Amongst suitable phenyl nuclei (1), there may especially be mentioned phenyl and the following groups:

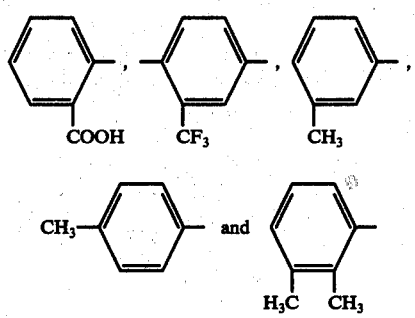

The following compounds are included among the sulphide compounds of the formula Ia (that is to say the compounds of the formula Ia wherein $y = 0$): ortho(2-morpholinoethylthio)-benzoic acid, N-[2-(phenylthio)-ethyl]-hexamethyleneimine, N-[2-(phenylthio)-ethyl]-pyrrolidine, N-[2-(phenylthio)-ethyl]-N'-ethoxycarbonylpiperazine, N-[2-(3-trifluoromethylphenylthio)-ethyl]-morpholine, N-[2-(3-methylphenylthio)-ethyl]-morpholine, N-[2-(4-methylphenylthio)-ethyl]-morpholine, N-[2-(2,3-dimethylphenylthio)-ethyl]-morpholine, 2-phenylthio-1-dimethylaminoethane, 2-phenylthio-1-diethylaminoethane, 2-phenylthio-1-dimethylaminopropane, N-[3-(phenylthio)-butyl]-piperidine, N-[3-phenylthio)-butyl]-pyrrolidine, N-[(3-phenylthio-2-methyl)-propyl]-piperidine, N-[(3-phenylthio-2-methyl)-propyl]-pyrrolidine, N-[3-(3-trifluoromethylphenylthio)-propyl]-pyrrolidine, N-[4-(phenylthio)butyl]-piperidine, N-[5-(phenylthio)-pentyl]-piperidine, N-[5-(phenylthio)-pentyl]-pyrrolidine, N-[4-(phenylthio)-butyl]-pyrrolidine and 2-phenylthio-1-(2-hydroxyethylamino)-ethane, and their addition salts.

The sulphide compounds of the formula Ia are useful both as intermediates in the synthesis of the sulphinyl compounds of the formula Ib, and as medicaments.

The sulphinyl derivatives of the formula Ia (that is to say the compounds of the formula Ia wherein $y = 1$) include the following products: ortho-(2-morpholinoethylsulphinyl)-benzoic acid, N-[2-(phenylsulphinyl-ethyl]-hexamethyleneimine (also called N-[2-(phenylsulphinyl)-ethyl]-azepine), N-[2-(phenylsulphinyl)-ethyl]-pyrrolidine, N-[2-(phenylsulphinyl)-ethyl]-N'-ethoxycarbonylpiperazine, N-[2-(3-trifluoromethylphenylsulphinyl)-ethyl]-morpholine, N-[2-(3-methylphenylsulphinyl)-ethyl]-morpholine, N-[2-(4-methylphenylsulphinyl)-ethyl]-morpholine, N-[2-(2,3-dimethylphenylsulphinyl)-ethyl]-morpholine, 2-phenylsulphinyl-1-dimethylaminoethane, 2-phenylsulphinyl-1-diethylaminoethane, 2-phenylsulphinyl-1-dimethylaminopropane, N-[3-(phenylsulphinyl)-butyl]-piperidine, N-[3-(phenylsulphinyl)-butyl]-pyrrolidine, N-[(3-phenylsulphinyl-2-methyl)-propyl]-piperidine, N-[(3-phenylsulphinyl-2-methyl)-propyl]-pyrrolidine, N-[3-(3-trifluoromethylphenylsulphinyl)-propyl]-pyrrolidine, N-[4-phenylsulphinyl)-butyl]butyl-piperidine, N-[5-phenylsulphinyl)-pentyl]-piperidine, N-[5-(phenylsulphinyl)-pentyl]-pyrrolidine, N-[4-phenylsulphinyl)-butyl]-pyrrolidine and 2-phenylsulphinyl-1-(2-hydroxyethylamino)-ethane and their addition salts.

The compounds according to the invention can be prepared by conventional reaction mechanisms; in particular, one of the techniques described in the earlier specification can be employed for their synthesis. The recommended method consists of preparing a sulphide compound (I, $y = 0$) and then oxidizing the said sulphide compound with $H_2O_2$ in the presence of acetic acid so as to give a sulphinyl compound (I, $y = 1$).

According to a feature of the invention, the compounds of formula I may be made by either (1) reacting together compounds of the formulae:

to produce a compound in which $y$ is 0, or (2) reacting together compounds of the formulae:

or (3) oxidizing a compound of the formula:

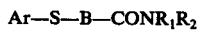

to produce a compound in which $y$ is 1, or (4) reducing a compound of the formula:

Ar—S—B—CONR$_1$R$_2$ where B is such that B-CH$_2$ is the same as Alk, to produce a compound in which $y$ is 0.

These various methods which are illustrated in the Examples given later, can be represented schematically as follows:

First method

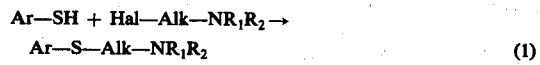

wherein Alk and NR$_1$R$_2$ are defined as above, Hal represents a halogen atom such as F, Cl, Br and I and preferably Cl and Br, and Z represents the nucleus (1) or the optionally substituted 2-benzimidazolyl group.

Second method

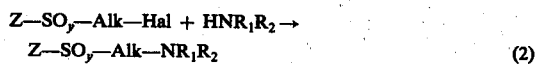

wherein $y$, Z, Alk, Hal and NR$_1$R$_2$ are defined as above. The starting material in which $y$ is 1 may be made by oxidation of the corresponding compound in which $y$ is 0.

Third method

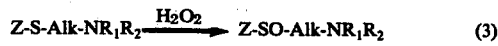

wherein Z, Alk, Hal and NR$_1$R$_2$ are deined as above.

Fourth method

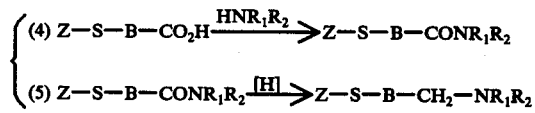

wherein Z and NR$_1$R$_2$ are defined as above and B is a C$_1$-C$_4$ hydrocarbon radical such that B—CH$_2$ represents Alk.

Of course, using these methods it is possible, on the one hand, to start from a starting mterial in which Ar is substituted and, on the other hand, to introduce the substituents of Ar after reactions 1, 2, 3, 4 or 5, without going outside the scope of the present invention.

The method recommended is that which comprises the reactions 1 and 3.

Preferably, in reaction 3, the oxidation of the sulphide is carried out with concentrated hydrogen peroxide, i.e. with hydrogen peroxide of at least 110 volumes strength (that is to say water containing at least 33% by weight of hydrogen peroxide). During this oxidation, it is necessary to avoid the formation of a relatively large quantity of the corresponding sulphonyl derivative. In practice, if the reaction is carried out at 100° C for 1 hour or more than 1 hour with hydrogen peroxide of 110-120 volumes strength, essentially only the said sulphonyl derivative is obtained and in order only to obtain the sulphinyl derivative the reaction is carried out either at 50° C for 1 hour followed by cooling if necessary and by maintaining the mixture at ambient temperature (15°-25° C) for several hours (especially for 1 to 3 hours or more), or at 37°-45° C (the temperature generally reached by the reaction mixture because the reaction is exothermic), followed by cooling and by maintaining the mixture at ambient temperature (15°-25° C) for 3 to 15 hours or more. It is possible to use approximately stoichiometric amounts of sulphide ($y = 0$) and of $H_2O_2$.

The addition salts with acids which can be prepared from the bases of the formula I can be obtained by a method which is in itself known, for example by reaction of the free base with an inorganic or organic acid. Amongst the acids which can be used there may especially be mentioned hydrochloric, hyrobromic, hydriodic, sulphuric, formic, maleic, fumaric, oxalic, ascorbic, citric, acetic, methanesulphonic, p-toluenesulphonic, lactic, succinic, benzoic, salicyclic, acetylsalicyclic, malic, tartaric, glutamic and aspartic acid.

The compounds of the present invention are useful in therapy, especially as analgesic and anti-inflammatory agents and/or agents which are active on the central nervous system. All the compounds are analgesic agents to a greateror less extent. Alongside this analgesic effect, certain products exhibit other interesting properties; thus, the product of Example 9 (CRL 40134) is an anti-inflammatory agent and the products of Examples 10 to 12(CRL 40188, CRL 40189 and CRL 40190, respectively) are active on the central nervous system and in particular act as anorexigenic substances.

The following Examples illustrate the invention. The products of the Examples are listed in Table I, where the sulphur arbitrarily occupies position 1 of the nucleus (1).

TABLE I

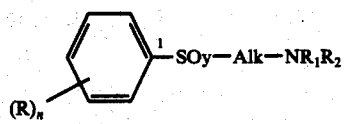

| Example | (R)$_n$ | y | Alk | NR$_1$R$_2$ | Acid addition salt | Melting point °C | Code No. |
|---|---|---|---|---|---|---|---|
| 1 | 2-COOH | 1 | CH$_2$CH$_2$ | morpholino | HCl | 150 (dec) | CRL 40047 |
| 2 | H | 1 | (CH$_2$)$_4$ | piperidino | HCl | 163–166 | CRL 40237 |
| 3 | H | 1 | CH$_2$CH$_2$ | azepino | HCl | 195 | CRL 40052 |
| 4 | H | 1 | CH$_2$CH$_2$ | pyrrolidino | HCl | 137 | CRL 40059 |
| 5 | H | 1 | CH$_2$CH$_2$ | —N⟨⟩N—CO$_2$C$_2$H$_5$ | HCl | 194 | CRL 40060 |
| 6 | 3-CF$_3$ | 1 | CH$_2$CH$_2$ | morpholino | HCl | 207–208 | CRL 40093 |
| 7 | 3-CH$_3$ | 1 | CH$_2$CH$_2$ | morpholino | HCl | 202 | CRL 40132 |
| 8 | 4-CH$_3$ | 1 | CH$_2$CH$_2$ | morpholino | HCl | 204 | CRL 40133 |
| 9 | 2,3-diCH$_3$ | 1 | CH$_2$CH$_2$ | morpholino | HCl | 246–248 | CRL 40134 |
| 10 | H | 1 | CH$_2$CH$_2$ | N(CH$_3$)$_2$ | HCl | 110–111 | CRL 40188 |
| 11 | H | 1 | CH$_2$CH$_2$ | N(C$_2$H$_5$)$_2$ | citrate | 90–95 | CRL 40189 |
| 12 | H | 1 | CH(CH$_3$)CH$_2$ | N(CH$_3$)$_2$ | HCl | 150–152 | CRL 40190 |
| 13 | H | 0 | CH$_2$CH$_2$ | NHCH$_2$CH$_2$OH | oxalate | 150–151 | CRL 40061 |
| 14 | H | 1 | CH(CH$_3$)CH$_2$CH$_2$ | piperidino | HCl | 160–162 | CRL 40230 |
| 15 | H | 0 | CH(CH$_3$)CH$_2$CH$_2$ | pyrrolidino | HCl | 138–139 | CRL 40231 |
| 16 | H | 1 | CH$_2$CH(CH$_3$)CH$_2$ | piperidino | HCl | 115–118 | CRL 40232 |
| 17 | H | 1 | CH$_2$CH(CH$_3$)CH$_2$ | pyrrolidino | HCl | 130–132 | CRL 40233 |
| 18 | 3-CF$_3$ | 1 | CH$_2$CH$_2$CH$_2$ | pyrrolidino | HCl | 144–146 | CRL 40235 |
| 19 | H | 1 | (CH$_2$)$_5$ | piperidino | HCl | 124–126 | CRL 40244 |
| 20 | H | 1 | (CH$_2$)$_5$ | pyrrolidino | citrate | 106–108 | CRL 40245 |
| 21 | H | 1 | (CH$_2$)$_4$ | pyrrolidino | citrate | 94–98 | CRL 40252 |
| 15 bis | H | 1 | CH(CH$_3$)CH$_2$CH$_2$ | pyrrolidino | HCl | — | CRL 40252 A |
| 13 bis | H | 1 | CH$_2$CH$_2$ | NHCH$_2$CH$_2$OH | oxalate | — | CRL 40061 A |

EXAMPLE 1

Ortho-(morpholinoethylsulphinyl)-benzoic acid hydrochloride

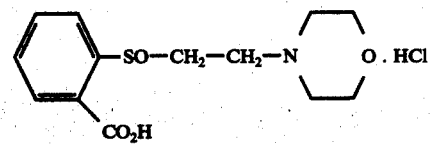

Code No. CRL 40,047 a. Preparation of ortho-(morpholinoethylthio)-benzoic acid hydrochloride 10 g (0.065 mol) of 2-mercaptobenzoic acid, 14.75 g (0.078 mol) of 2-chloroethylmorpholine hydrochloride, 8.4 g (0.21 mol) of NaOH pellets and 75 ml of demineralised water are introduced into a 250 ml single-neck flask equipped with a condenser.

The limpid solution obtained is heated to the reflux temperature for 2 hours and then acidified with concentrated hydrochloric acid at ordinary temperature, namely 15°–25° C. After washing with ether, the water is evaporated under reduced vacuum and the residue is taken up in 100 ml of boiling methanol; the insoluble matter is filtered off and the methanol is in turn evaporated. After recrystallisation from 60 ml of water, 15.9 g of ortho-(morpholinoethylthio)-benzoic acid hydrochloride melting at 200° C are obtained. Yield = 79%.

b. CRL 40,047

15 g (0.0495 mol) of the sulphide previously prepared are oxidised at 50° C for 1 hour by means of 4.95 ml (0.0495 mol) of hydrogen peroxide of 110 volumes strength in 75 ml of acetic acid. When the reaction has ended, The reaction mixture is kept at 5° C for 12 hours and the oxidised product is then filtered off, dried and thereafter recrystallised from 100 ml of ethanol; this gives 11 g of CRL 40,047. Yield = 69.5%. Melting point = 150° C (with decomposition).

Analysis: Chlorine determination (Volhard) calculated = 11.1%; Found = 10.6%

EXAMPLE 2

N-[4-(Phenylsulphinyl)-butyl]-piperidine hydrochloride

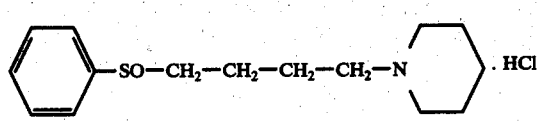

Code No. CRL 40,237 a. Preparation of 1-phenylthio-4-chloro-butane 11 g (0.1 mol) of thiophenol and 18.9 g (0.11 mol) of 1-bromo-4-chlorobutane are mixed at ordinary temperature in a 250 ml flask equipped with a condenser, a thermometer and a dropping funnel. 100 ml of ethanol are added, the mixture is heated to 40° C and 20 ml of 5N NaOH are then added dropwise at this temperature. The speed of addition of the sodium hydroxide is regulated so as to have a reaction medium of neutral pH. When the addition is complete, the reactants are left in contact at 40° C for 3 hours, the alcohol is then evaporated, the oil is extracted with ether and the ether solution is washed with 2N NaOH and then with water. Thereafter the organic phase is dried over MgSO$_4$, the ether is evaporated and a yellow oil ia obtained, which crystallises from ethanol. (18.4 g; 0.092 mol; yield: about 92%).

b. Preparation of N-[4-(phenylthio)-butyl]-piperidine hydrochloride

A solution of 0.46 mol of Na$_2$CO$_3$ in 470 ml of water is mixed with 0.133 mol(13.3 ml) of piperidine in a 1 liter three-neck flask. The mixture is heated to the reflux temperature and 0.092 mol of the chlorinated derivative obtained in a), dissolved in hot ethanol, is added dropwise at the boil. When the addition is complete, the mixture is left under reflux for at least 8 hours and is then cooled, the ethanol is evaporated, the oil is extracted with ether, the ether solution is washed repeatedly with water until the ph of the wash waters is neutral and is then extracted with 2N HCl, the acid solution is washed with ether, the base is precipitated by addition of concentrated NaOH and extracted with ether, the ether solution is washed with water and dried over $Na_2SO_4$, the ether is evaporated and 11.7 g of base (a yellow oil) are obtained.

The hydrochloride is precipitated in ethyl acetate by adding a solution of hydrogen chloride in ethanol, and 13.1 g of hydrochloride are obtained. Melting point = 143°–144° C. The yield relative to the thiophenol starting material is about 46%.

c. CRL 40,237

13.1 g (0.046 mol) of the above hydrochloride are oxidised with 4.2 ml of $H_2O_2$ of 124 volumes strength in 50 ml of $CH_3COOH$. After 1 hour 30 minutes at 40°–45° C, the acetic acid is evaporated and the CRL 40,237 is crystallised from ethyl acetate and recrystallised from acetone. This gives 11.5 g of CRL 40,237. This is a white powder whic is very soluble in water and alcohols and melts at 163°–166° C. The overall yield is 38%.

EXAMPLE 3

N-[2-(Phenylsulphinyl)-ethyl]-azepine hydrochloride

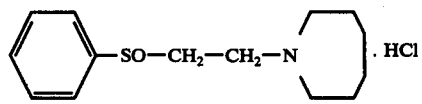

Code No. CRL 40,052

31.8 g (0.3 mol) of sodium carbonate, 200 ml of water, 18.85 g (0.1 mol) of 2-chloro-1-phenylsulphinylethane, 9.9 g (0.1 mol) of azepine and 120 ml. of ethanol are introduced into a 1 liter three-neck flask equipped with a stirrer and a condenser.

After heating under reflux for 6 hours, the ethanol is evaporated under reduced vacuum and the supernatant oil is then extracted with 2 × 100 ml of ethyl acetate. The mixture is decanted and the organic phase is then extracted with about 3N hydrochloric acid. The aqueous phase obtained is rendered alkaline with sodium hydroxide solution whilst cooling on an ice bath and is then extracted with ethyl acetate. After washing with water, the organic phase is dried over magnesium sulphate and the solvent is then evaporated. This gives 26 g of N-[2-(phenylsulphinyl)-ethyl]-azepine. The base obtained is taken up in isopropanol and the hydrochloride is precipitated by adding a solution of hydrogen chloride in ether. This gives, after recrystallisation from 100 ml of isopropanol, 22.3 g of CRL 40,052, melting at 195° C.

Yield = 78%.

EXAMPLE 4

N-[2-(Phenylsulphinyl)-ethyl]-pyrrolidine hydrochloride

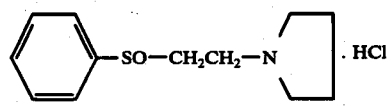

Code No. CRL 40,059

31.8 g (0.3 mol) of pure and dry sodium carbonate, 200 ml of demineralised water, 18.85 g (0.1 mol) of 2-chloro-1-phenylsulphinyl-ethane, 7.8 g (0.11 mol) of pyrrolidine and 120 ml of ethanol are introduced into a 500 ml three-neck flask equipped with a mechanical stirrer and a condenser.

The reaction mixture is kept at the reflux temperature of the ethanol-water azeotrope for 4 hours and the solvents and the excess pyrrolidine are then evaporated in vacuo. The evaporation residue is taken up in 250 ml of diethyl ether. The solution is filtered and then dried over sodium sulphate. After acidification with a solution of hydrogen chloride in ethanol, N-[2-(phenylsulphinyl)-ethyl]-pyrrolidine hydrochloride is filtered off and then dried.

Purification: the product obtained is taken up in 250 ml of acetone, the mixture is raised to the reflux temperature and isopropanol is then added until all has dissolved. The mixture is filtered through charcoal and is then left to recrystallise for 24 hours at 5° C. This gives 12.7 g of CRL 40059 melting at 137° C (hygroscopic white powder).

Analysis:
Chlorine determination: calculated = 13.7% found = 13.8%

EXAMPLE 5

N-[2-(Phenylsulphinyl)-ethyl]-N'-carboethoxy-piperazine hydrochloride

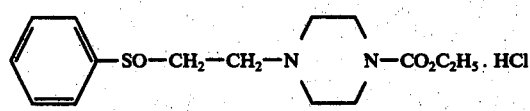

Code No. CRL 40,060

24 g (0.225 mol) of sodium carbonate, 15.1 g (0.08 mol) of 2-chloro-1-phenylsulphinyl-ethane, 14.6 g (0.075 mol) of monocarbethoxypiperazine hydrochloride, 55 ml of ethanol and 200 ml of demineralised water are introduced into a 500 ml single-neck flask equipped with a magnetic stirrer and surmounted by a condenser.

The limpid solution obtained is heated for 8 hours to the reflux temperature and the ethanol is then evaporated in vacuo; the supernatant oil is extracted with ethyl acetate. The mixture is decanted and the organic phase is then again extracted with 3N hydrochloric acid. The aqueous phase is rendered alkaline with sodium carbonate and extracted with ethyl acetate, and the extract is dried over magnesium sulphate and then evaporated to dryness. This gives 23.9 g of N-[2-(phenylsulphinyl)-ethyl]-N'-carbethoxypiperazine base melting at 76° C after recrystallisation from a cyclohexane-benzene mixture.

The hydrochloride, prepared in isopropanol by reaction with a solution of hydrogen chloride in ethanol followed by recrystallisation from 240 ml of isopropanol, gives 24 g of CRL 40,060 melting at 194° C. Yield = 92%.

Analysis:

Chlorine determination (Volhard): calculated = 10.5% found = 10.5%

EXAMPLE 6

N-[2-(3-Trifluoromethylphenylsulphinyl)-ethyl]-morpholine hydrochloride

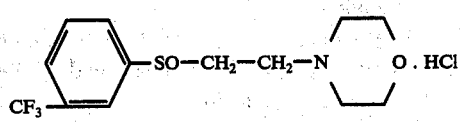

Code No. CRL 40,093 a. N-[2-(3-Trifluoromethylphenylthio)-ethyl]-morpholine hydrochloride.

20 g (0.1 mol) of 2-chloroethylmorpholine hydrochloride are added to a violently stirred solution of 17.8 g (0.1 mol) of meta-trifluoromethylbenzene-thiol and 8 g (0.2 mol) of NaOH pellets in 50 ml of water at 75°-80° C, and the mixture is heated for 15 minutes to the reflux temperature, cooled and extracted with ether. The ether solution is extracted with 100 ml of 2N HCl and the base is precipitated with NaOH and extracted with ether. The extract is dried over magnesium sulphate and filtered, a solution of hydrogen chloride and ethanol is added to the filtrate until the pH is acid, and the product is filtered off. 29 g (89%) of the stated hydrochloride are obtained. Melting point = 166°-167° C.

b. CRL 40,093

14.7 g (0.045 mol) of the hydrochloride obtained above, in solution in 45 ml of acetic acid, are oxidised with 4.5 ml (0.045 mol) of hydrogen peroxide of 110 volumes strength. After 1 hour at 50° C, the solution is evaporated to dryness in vacuo and the residue is taken up in 100 ml of acetone and filtered off. It is recrystallised from methanol and CRL 40,093 is obtained in a yield of 70%. It is in the form of small white crystals. It is soluble in water and methanol, slightly soluble in ethanol and insoluble in acetone and ether. It melts at 207°-208° C.

EXAMPLES 7 to 13

Following the procedure indicated in Example 6, starting from the following thiols: 3-methylphenylthiol, 4-methylphenylthiol, 2,3-dimethylthiol and thiophenol, and from the chloroamines: 2-chloroethylmorpholine, 2-chloro-1-(N,N-dimethylamino)-ethane, 2-chloro-1-(N,N-diethylamino)-ethane, 2-chloro-1(N,N-dimethylamino)-propane and 2-chloro-1-(2-hydroxyethylamino)-ethane, the following products were obtained: N-[2-(3-methylphenylthio)-ethyl]-morpholine hydrochloride, melting point = 140° C, yield: 89%; N-[2(4-methylphenylthio)-ethyl]-morpholine hydrochloride, melting point = 169° C, yield: 71%; N-[2-(2,3-dimethylphenylthio)-ethyl]-morpholine hydrochloride, melting point = 191° C, yield: 86%; 2-phenylthio-1-dimethylaminoethane hydrochloride, melting point = 113° C, yield: 90%; 2-phenylthio-1-diethylaminoethane hydrochloride, melting point = 96°-97° C, yield about 65%; 2-phenylthio-1-dimethylaminopropane hydrochloride, melting point = 137° C and 2-phenylthio-1-(2-hydroxyethylamino)ethane hydrochloride, melting point = 108° C, yield 99%. From these, the following compounds were obtained:

CRL 40,132: N-[2-(3-methylphenylsulphinyl)-ethyl]-morpholine hydrochloride, melting point = 202° C, yield: 77%.

CRL 40,133: N-[2-(4-methylphenylsulphinyl)-ethyl]-morpholine hydrochloride, melting point = 204° C, yield: 77%.

CRL 40,134: N-[2-(2,3-dimethylphenylsulphinyl)-ethyl]-morpholine hydrochoride, melting point = 246°-248° C, yield: 72%.

CRL 40,188: 2-phenylsulphinyl-1-dimethylaminoethane hydrochloride, melting point = 110°-111° C, yield: 90%.

CRL 40,189: 2-phenylsulphinyl-1-diethylaminoethane citrate, melting point = 90°-95° C, yield: 52%.

CRL 40,190: 2-phenylsulphinyl-1-dimethylaminopropane hydrochloride, melting point = 150°-152° C, yield: 56%.

CRL 40,061: 2-phenylthio-1-(2-hydroxyethylamino)-ethane oxalate, melting point = 150°-151° C, yield: 61.7%.

EXAMPLE 13 bis

Following the mechanism of reactions 3 and 4, the sulphinyl derivative (y = 1) homologous to the product of Example 13 (CRL 40,061), namely 2-phenylsulphinyl-1-(2-hydroxyethylamino)-ethane is obtained, which in the form of the oxalate has the Code No. CRL 40,061A.

EXAMPLE 14

N-]3-(Phenylsulphinyl)-butyl]-piperidine hydrochloride

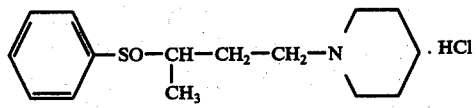

Code No. CRL 40,230 a. 3-(Phenylthio)-butyric acid 0.25 g of sodium in small pieces, in 50 ml (0.5 mol) of thiophenol, is heated to 90°-95° C whilst stirring, and 52.5 ml (0.55 mol) of methyl crotonate are added dropwise. The mixture is heated further for 1 hour at 120° C and 85 g (boiling point/5 mm Hg = 137°-138° C) of the resulting ester are distilled in vacuo. 53 g (0.25 mol) of this ester in solution in 200 ml of methanol are hydrolysed with 16 g (0.4 mol) of NaOH in 200 ml of water. The mixture is heated for 2 hours under reflux, the alcohol is evaporated in vacuo, the residue is taken up in water and the product is precipitated with concentrated HCl and extracted with ether. The extract is washed with water and dried, and 32 g (65%) of a white oil are obtained.

b. Piperidine amide of 3-(phenylthio)-butyric acid 21 g of the acid obtained in (a) are heated for 2 hours to the reflux temperature with 30 ml of thionyl chloride, the mixture is evaporated to dryness in vacuo, the residue is taken up in ether, the solution is filtered through charcoal and the filtrate is added dropwise to a solution of 20 g (0.25 mol) of piperidine in 100 ml of ether. The mixture is stirred for 2 hours at ambient temperature, washed with water, dilute HCl, dilute bicarbonate and again with water, dried and evaporated in vacuo. 22 g of a yellow oil are obtained.

c. N-[3-(Phenylthio)-butyl]-piperidine hydrochloride 18.1 g (0.069 mol) of the above amide dissolved in 100 ml of anhydrous ether are added dropwise, at the reflux temperature, to a stirred suspension of 4 g (0.1 mol) of LiAlH$_4$ in 200 ml of anhydrous ether. The mixture is kept at the reflux temperature for 2 hours and is then left to stand for 24 hours. 20 ml of water are added dropwise and the product is filtered off and acidified with a solution of hydrogen chloride in ether. The resulting product is filtered off and recrystallised from acetone. 12.2 g (62%) of the expected hydrochloride are obtained. Melting point = 143°–144° C.

d. CRL 40,230

11.5 g (0.04 mol) of the preceding hydrochloride, dissolved in 40 ml of acetic acid, are oxidised with 4 ml of hydrogen peroxide of 110 volumes strength. After standing overnight, the mixture is evaporated to dryness in vacuo and the residue is crystallised from ethyl acetate. CRL 40,230 is obtained in a yield of 28%. It is in the form of slightly hygroscopic small white crystals. Melting point = 160°–162° C.

EXAMPLE 15

N-[3-(Phenylthio)-butyl]-pyrrolidine hydrochloride

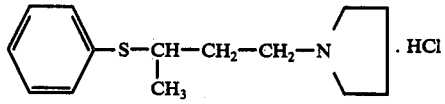

Code No. CRL 40,231 a. N-[(3-Phenylthio)-butyryl]-pyrrolidine

A solution of 32.5 g (0.15 mol) of 3-phenylthiobutyryl chloride (see preparation of CRL 40,230) in ether is prepared and is added dropwise to a solution of 28 g (0.4 mol) of pyrrolidine in 200 ml of ether. The mixture is stirred for 2 hours and is washed with water with 2N HCl, with dilute bicarbonate and then with water. It is dried and evaporated to dryness in vacuo. 25 g (65%) of a white oil are obtained.

b. CRL 40,231

25 g (0.096 mol) of N-[(3-phenylthio)butyryl]-pyrrolidine dissolved in 100 ml of anhydrous ether are added dropwise to a suspension of 6 g (0.15 mol) of LiAlH$_4$ in 300 ml of anhydrous ether at the reflux temperature. The mixture is heated at the reflux temperature for 3 hours and left overnight at ambient temperature. 30 ml of water are added in the cold, the mixture is filtered, the residue is washed with ether, the filtrate is acidified with a solution of hydrogen chloride in ether and the product is filtered off. It is recrystallised from isopropanol.

CRL 40,231 is obtained in a yield of 60%; it is a white powder which is soluble in water, methanol and ethanol and insoluble in acetone and ether. It melts at 138°–139° C.

EXAMPLE 15bis

N-[3-(Phenylsulphinyl)-butyl]-pyrrolidine hydrochloride

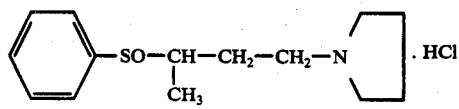

Code No. CRL 40,231A

CRL 40,231 is converted to the corresponding sulphinyl derivative by following the procedure indicated in Example 14 (paragraph d).

EXAMPLE 16

N-[3-Phenylsulphinyl-2-methyl)-propyl]-piperidine hydrochloride

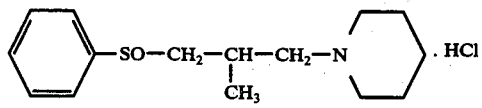

Code No. CRL 40,232 a. 1-Phenylthio-2-methyl-3-chloropropane

A mixture of 22 g (0.2 mol) of thiophenol and 37.7 g (0.22 mol) of 3-bromo-1-chloro-2-methylpropane in 200 ml of ethanol is stirred at 40° C and 40 ml (0.2 mol) of 5N sodium hydroxide solution is added dropwise. The mixture is stirred for a further 2 hours at 40° C and evaporated to dryness in vacuo, the residue is extracted with methylene chloride and the extract is washed with water, dried and evaporated in vacuo. 39 g (97%) of a yellow oil are obtained.

b. N-[(3-Phenylthio-2-methyl)-propyl]-piperidine hydrochloride

A mixture of 17 g (0.2 mol) of piperidine, 30 g (0.3 mol) of sodium carbonate, 120 ml of water and 120 ml of ethanol is heated to the reflux temperature. 18 g (0.09 mol) of 1-phenylthio-2-methyl-3-chloropropane dissolved in 50 ml of ethanol are added dropwise. After refluxing for 5 hours, the alcohol is evaporated in vacuo, the residue is extracted with ether, the extract is washed 3 times with water and extracted with 200 ml of 1N HCl, the product is precipitated with concentrated NaOH and extracted with ether, and the extract is washed with water and dried. The ether is evaporated in vacuo, 100 ml of ethyl acetate and sufficient of a solution of hydrogen chloride in ether to give an acid pH are added, and the product is filtered off. It is recrystallised from acetone. 14.5 g of hydrochloride (57%) are obtained. Melting point 108–110° C.

c. CRL 40,232

13.2 g (0.046 mol) of the hydrochloride obtained above, dissolved in 45 ml of acetic acid, are treated with 4.6 ml of hydrogen peroxide of 110 volumes strength. After 1 hour at 50° C, the mixture is evaporated to dryness in vacuo and the residue is crystallised from ethyl acetae. CRL 40,232 is obtained in a yield of 44%. It is in the form of hygroscopic white crystals. Melting point 115°–118° C.

EXAMPLE 17

N-[(3-Phenylsulphinyl-2-methyl)-propyl]-pyrrolidine hydrochloride

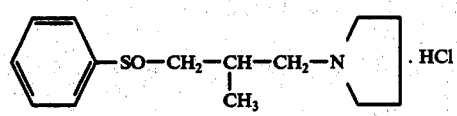

Code No. CRL 40,233 a. N-[(3-Phenylthio-2-methyl)-propyl]-pyrrolidine hydrochloride 20 g (0.1 mol) of 1-phenylthio-2-methyl-3-chloropropane (compare preparation of CRL 40,232) dissolved in 50 ml of ethanol and are added dropwise, whilst stirring, to a refluxing solution of 14.2 g (0.2 mol) of pyrrolidine, 30 g (0.3 mol) of sodium carbonate, 160 ml of ethanol and 160 ml of water. After refluxing for 3 hours, the alcohol is evaporated, the residue is extracted with ether and the ether solution is extracted with 1N HCl. The base is precipitated with concentrated NaOH and extracted with ether, and the extract is washed with water and dried. The ether is evaporated, 100 ml of ethyl acetate are added and the mixture is acidified with a solution of hydrogen chloride in ether. The product is recrystallised from methyl ethyl ketone. 14 g (52%) are obtained. Melting point 92°–93° C.

b. CRL 40,233

12 g (0.042 mol) of the hydrochloride obtained above are oxidised with 4.2 ml of hydrogen peroxide of 110 volumes strength in solution in 40 ml of acetic acid. After 1 hour at 50° C, the mixture is evaporated to dryness in vacuo and the residue is taken up in ethyl acetate and filtered off.

CRL 40,233 is obtained in a yield of 40%. It is in the form of hygroscopic white crystals. Melting point 130°–132° C.

EXAMPLE 18

N-[3-(3-Trifluoromethylphenylsulphinyl)-propyl]-pyrrolidine hydrochloride

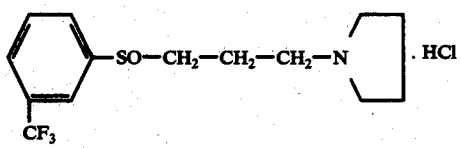

Code No. CRL 40,235 a. N-[3)3-Trifluoromethylphenylthio)-propyl]-pyrrolidine 17.8 g (0.1 mol) of 3-trifluoromethylthiophenol and a solution of 4 g (0.1 mol) of NaOH in 100 m³ of water are introduced into a 250 cm³ three-neck flask equipped with a condenser, a thermometer, a dropping funnel and a magnetic stirrer. The mixture is heated to 60° C and 17.7 g (0.12 mol) of N-(3-chloropropyl)-pyrrolidine are then added dropwise.

The mixture is then heated to the reflux temperature for 2 hours and cooled, the oil is extracted with ether, the extract is washed with water and the ether phase is then collected and extracted with 2N HCl. After washing the acid solution with ether, the base is precipitated by adding concentrated NaOH and is then extracted with ether.

The ether solution is washed with water until the pH of the wash water is neutral, and is dried over Na$_2$SO$_4$, the ether is evaporated and 26.1 g (0.09 mol) of a yellow oil are obtained; yield relative to the thiophenol starting material: 90%.

b. CRL 40,235

Starting from 22.1 g (0.0765 mol) of the base obtained above, the corresponding hydrochloride is prepared in a solution of hydrogen chloride in ethanol, the ethanol is evaporated to dryness, and 80 ml of CH$_3$COOH and 7 ml of H$_2$O$_2$ of 124 volumes strength are added at 20° C. The temperature rapidly reaches 45°–50° C ad stays thereat for about 1 hour. The acetic acid is then evaporated and the CRL 40,235 is crystallised from ethyl acetate. It is recrystallised from acetone and 22.9 g are obtained. Melting point 144°–146° C. Yield from stage b: 87%. Overall yield relative to the thiophenol of stages a and b: 66.5%.

EXAMPLE 19

N-[(5-Phenylsulphinyl)-pentyl]-piperidine hydrochloride

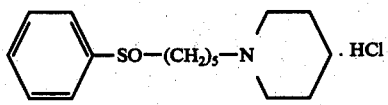

Code No. CRL 40,244 a. 5-Bromo-1-phenylthiopentane

A solution of 20 ml (0.2 mol) of thiophenol and 50.6 g (0.22 mol) of 1,5-dibromopentane in 200 ml of ethanol is heated to 40° C whilst stirring and 40 ml (0.2 mol) of 5N NaOH are added dropwise. Thereafter the mixture is stirred for 2 hours and after standing overnight the alcohol is evaporated in vacuo, the residue is extracted with methylene chloride and the extract is washed 3 to 4 times with water, dried and evaporated. A yellow oil is obtained in quantitative yield.

b. N-[(5-Phenylthio)-pentyl]-piperidine hydrochloride

A mixture of 17 g (0.2 mol) of piperidine, 20 g (0.2 mol) of sodium carbonate in 120 ml of water and 100 ml of ethanol is stirred at the reflux temperature and 26 g (0.1 mol) of 5-bromo-1-phenylthiopentane dissolved in 50 ml of ethanol are added dropwise. After 8 hours at the reflux temperature the mixture is evaporated in vacuo. The base is extracted with ether, the ether is washed three times with water and the hydrochloride is precipitated with 4N HCl. The product is filtered off and recrystallised from acetone. 18 g (60%) are obtained. Melting point 135–136° C.

c. CRL 40,244

12 g (0.04 mol) of the sulphide obtained above are oxidised with 4 ml of hydrogen peroxide of 110 volumes strength in 40 ml of acetic acid. The mixture is evaporated in vacuo, the residue is taken up in ethyl acetate and the product is filtered off and recrystallised from acetone. CRL 40,244 is obtained in a yield of 48%. Melting point 124°–126° C.

EXAMPLE 20

N-[(5-Phenylsulphinyl)-pentyl]-pyrrolidine citrate

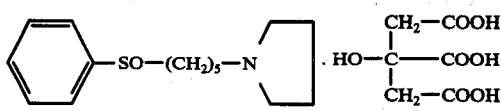

Code No. CRL 40,245 a. N-[(5-Phenylthio)-pentyl]-pyrrolidine hydrochloride

A mixture of 14.2 g (0.2 mol) of pyrrolidine, 20 g of Na$_2$CO$_3$ in 150 ml of water and 120 ml of ethanol is heated to the reflux temperature whilst stirring, and 26 g (0.1 mol) of 5-bromo-1-phenylthiopentane dissolved in 50 ml of ethanol are then added dropwise over the course of 2 hours. After 6 hours at the reflux temperature, the alcohol is evaporated in vacuo, the residue is extracted with ethyl acetate, the extract is washed 3 times with water and the hydrochloride is precipitated with 2N HCl. The product is filtered off and recrystallised from isopropanol. 13.8 g (48%) are obtained. Melting point 123° C.

b. CRL 40,245

4.7 ml of hydrogen peroxide of 110 volumes strength are added to a solution of 13.5 g (0.047 mol) of N-[(5-phenylthio)-pentyl]-pyrrolidine hydrochloride in 50 ml of acetic acid. After 1 hour at 50° C, the mixture is evaporated in vacuo. 100 ml of water are added, the product is precipitated with concentrated NaOH and extracted with ether, and the extract is dried and evaporated in vacuo. The 12 g (0.045 mol) of base are dissolved in 50 ml of acetone and a solution of 9.5 g (0.045 mol) of citric acid dissolved in (sic) 100 ml of acetone is added. The product is filtered off, washed with acetone and recrystallised from ethanol.

CRL 40,245 is obtained in a yield of 45%. Melting point 106°-108° C.

EXAMPLE 21

N-[(4-Phenylsulphinyl)-butyl]-pyrrolidine citrate

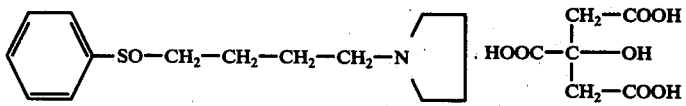

Code No. CRL 40,252 a. N-[(4-Phenylthio)-butyl]-pyrrolidine hydrochloride

A solution of 0.92 mol of Na$_2$CO$_3$ dissolved in 800 ml of hot water, and 0.3 mol (25 ml) of pyrrolidine, are mixed in a 2 liter three-neck flask. The mixture is heated to the reflux temperature and 0.2 mol (40 g) of 1-phenylthio-4-chlorobutane dissolved in hot ethanol is added dropwise at the boil.

When the addition is complete, the mixture is left at the reflux temperature for at least 8 hours and is then cooled, the ethanol is evaporated, the oil is extracted with ether, the extract is washed with water until the pH of the wash waters is neutral and is then extracted with 2N HCl, the acid solution is washed with ether, the base is precipitated by adding concentrated NaOH and is extracted with ether, the ether extract is washed with water and dried over Na$_2$SO$_4$, the ether is evaporated and 21.4 g of a base (light yellow oil) are obtained.

The corresponding hydrochloride is precipitated by adding a solution of hydrogen chloride in ethanol to a solution of the base in ethyl acetate. Thereafter it is recrystallised from ethyl acetate and 24.0 g of N-[(4-phenylthio)-propyl]-pyrrolidine hydrochloride are obtained. Melting point 100° C.

b. CRL 40,252

24.0 (0.088 mol) of the preceding hydrochloride are oxidised with 8 ml of H$_2$O$_2$ (124 volumes strength) in 80 ml of CH$_3$COOH. The mixture is left at 40°-45° C for about 1 hour 30 minutes, the acetic acid is evaporated and the hydrochloride is precipitated in ether. The crystallisation is slow and as the product obtained proves to be extremely hygroscopic, it is dissolved in water, the solution is neutralised by adding concentrated NaOH and the corresponding base is extracted with ether.

The ether solution is washed with water and then dried over Na$_2$SO$_4$ and evaporated; 20.1 g of base (oil) are obtained.

The yield of the oxidation is about 90%. The citrate is prepared by adding 19 g (a slight excess) of citric acid dissolved in 30 ml of ethanol to 20.1 g of the pure base. After adding 200 ml of acetone to the preceding solution, CRL 40,252 crystallises slowly in the cold. 34.5 g of CRL 40,252 are thus obtained. Melting point 94°-98° C.

EXAMPLE 22

1-(p-Chlorobenzoyl)-2-(2-morpholinoethylsulphinyl)-benzimidazole hydrochloride.

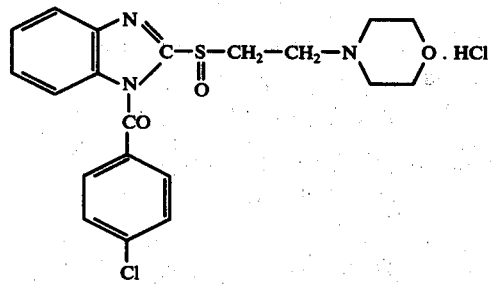

Code No. CRL 40,053

3.55 g (0.02 mol) of para-chlorobenzoyl chloride are added dropwise at between + 5 and + 10° C to a stirred solution of 5.6 g (0.02 mol) of 2-(2'-morpholinoethylsulphinyl)-benzimidazole (prepared as indicated in Example 14 and 14 bis of French Application No. 72/33,005) in 60 ml of pyridine. The mixture is stirred for one hour and is left overnight at ambient temperature (15°-25° C). The pyridine is evaporated in vacuo and the residue is taken up in 100 ml of water and filtered off. The precipitate is taken up in 2N hydrochloric acid. The solution is filtered and the filtrate is precipitated by means of sodium carbonate; the product is filtered off, washed with water and dried. 4.8 g of the free base are obtained. Melting point = 125°-126° C.

The base, dissolved in ethanol, is acidified with a solution of hydrogen chloride in ethanol, the product is filtered off and recrystallised from methanol. 1-p-Chlorobenzoyl-2-(2'-morpholinoethylsulphinyl)-benzimidazole hydrochloride is obtained in a yield of 52%. This product is in the form of small white needles melting at 192°–195° C; it is soluble in water, sparingly soluble in cold methanol and insoluble in ethanol, acetone and ether.

The results of the pharmacological tests which have been carried out are summarised below.

CRL 40,047 (the product of Example 1) has a low toxicity when orally administered to mice; the LD-0 is 4,000 mg/kg and the LD-50 is greater than 6,000 mg/kg.

CRL 40,052 (the product of Example 3), when orally administered to mice, shows a LD-0 of less than 250 mg/kg and a LD-50 of 480 mg/kg.

CRL 40,060 (the product of Example 5), when orally administered to mice, shows a LD-0 of 500 mg/kg and a LD-50 of 1,550 mg/kg.

CRL 40,059 (the product of Example 4), when orally administered to mice, shows a LD-0 of 200 mg/kg and a LD-50 of 360 mg/kg. It furthermore has an anorexigenic effect.

CRL 40,093 (the product of Example 6), when orally administered to mice, shows a LD-0 of 750 mg/kg and a LD-50 of 1,450 mg/kg. This product has an analgesic effect at orally administered doses of 58 mg/kg upwards, according to the acetic acid test, and at orally administered doses of 89 mg/kg upwards, according to the acetyl choline test. It does not have an anti-oedematous action.

CRL 40,132 (the product of Example 7) has a low toxicity. When orally administered to mice it exhibits a LD-0 of 1,000 mg/kg and a LD-50 greater than 3,000 mg/kg. It has an analgesic effect at an orally administered dose of 50 mg/kg upwards according to the acetic acid test and at an orally administered dose of 100 mg/kg upwards according to the acetylcholine test. It does not have an anti-oedematous action.

CRL 40,133 (the product of Example 8) is of low toxicity. When orally administered to mice it exhibits a LD-0 of 1,000 mg/kg and a LD-50 of about 2,000 mg/kg. It has an analgesic action at an orally administered dose of 200 mg/kg according to the acetic acid test but on the other hand does not possess an anti-oedematous effect. CRL 40,132 furthermore exhibits an anorexigenic effect.

CRL 40,134 (the product of Example 9), when orally administered to mice, exhibits a LD-0 of 1,000 mg/kg and a LD-50 of 1,800 mg/kg. It has an analgesic action at an orally administered dose of 36 mg/kg according to the acetic acid test and at an orally administered dose of 90 mg/kg according to the acetylcholine test. It furthermore exhibits an anti-oedematous action at an orally administered dose of 180 mg/kg according to the carraghenine test.

CRL 40,188 (the product of Example 10), when intraperitoneally administered to mice exhibits a LD-0 of less than 512 mg/kg (the product being administered in solution in a volume of 20 ml/kg). CRL 40,188, at intraperitoneally administered doses of 2 mg/kg, 8 mg/kg and 32 mg/kg in mice produces an increase in the reactivity to touch and in the agressivity reaction. In rats, under the same conditions, the same phenomena are observed at intraperitoneally administered doses of 4 mg/kg upwards. Furthermore, in mice and rats, a moderate boosting of the amphetamine standard effect is observed. This product exhibits an anorexigenic action which at the test dose used is a little less intense than that of fenfluramine (an anorexigenic reference substance).

CRL 40,189 (the product of Example 11), when intraperitoneally administered to mice, exhibits a LD-0 of less than 500 mg/kg. It is found that this product acts as a moderate excitation agent on the animal at doses of 16 mg/kg upwards. It produces a boosting of the standard effects caused by amphetamine in rats, when intraperitoneally administered at doses of 8 mg/kg upwards. It exhibits an anorexigenic action which at the test dose used is a little less intense than that of fenfluramine.

CRL 40,190 (the product of Example 12), exhibits an anorexigenic action more intense than that of fenfluramine.

CRL 40,053 (the product of Example 22), when orally administered to mice, exhibits a LD-0 of 500 mg/kg and a LD-50 of 1,100 mg/kg. In mice, it has an analgesic action at an orally administered dose of 44 mg/kg according to the acetic acid test and at an orally administered dose of 110 mg/kg according to the acetylcholine test. On the other hand, it does not exhibit an anti-oedematous action according to the carragheenin oedema test.

The clinical tests have confirmed the pharmacological tests, especially as regards the analgesic property which is a feature shown by all the products of the series. Furthermore, CRL 40,189 and 40,190 have given good results in man as anorexigenic agents after administration of either of them in the form of tablets each containing 0.05 g of active ingredient, the posology being 1 tablet 2 hours before the two principal daily meals.

According to the invention, therapeutic compositions are recommended which contain at least one compound of the formula I or one of its non-toxic addition salts in association with a physiologically acceptable excipient.

We claim:

1. A therapeutic composition comprising an anorectically effective amount of 2-phenylsulphinyl-1-diethylaminoethane citrate in association with a physiologically acceptable excipient.

2. A therapeutic composition comprising an anorectically effective amount of 2-phenylsulphinyl-1-dimethylaminopropane hydrochloride in association with a physiologically acceptable excipient.

* * * * *